United States Patent
Al-Saffar

(10) Patent No.: US 12,216,097 B2
(45) Date of Patent: Feb. 4, 2025

(54) SAMPLE CYLINDER CONTENT IDENTIFICATION SYSTEM AND METHOD THEREOF

(71) Applicant: SAUDI ARABIAN OIL COMPANY, Dhahran (SA)

(72) Inventor: Ahmad Saeed Al-Saffar, RT Northern Area (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 45 days.

(21) Appl. No.: 17/704,363

(22) Filed: Mar. 25, 2022

(65) Prior Publication Data

US 2023/0304973 A1    Sep. 28, 2023

(51) Int. Cl.
*G01N 30/14*    (2006.01)
*G01N 33/00*    (2006.01)
*G01N 30/02*    (2006.01)

(52) U.S. Cl.
CPC ......... *G01N 30/14* (2013.01); *G01N 33/0044* (2013.01); *G01N 2030/025* (2013.01)

(58) Field of Classification Search
CPC .................................................. G01N 33/0044
See application file for complete search history.

(56) References Cited

U.S. PATENT DOCUMENTS

| | | | |
|---|---|---|---|
| 4,443,418 A | * | 4/1984 | Lutz .................. B01D 53/1493 562/572 |
| 6,939,717 B2 | | 9/2005 | Jiang et al. |
| 8,347,688 B2 | | 1/2013 | O'Brien |
| 10,494,919 B2 | | 12/2019 | Smith |
| 11,167,242 B1 | | 11/2021 | Parker et al. |
| 2015/0167455 A1 | | 6/2015 | Irani |

FOREIGN PATENT DOCUMENTS

| | | | |
|---|---|---|---|
| JP | H07122525 | * | 5/1995 |
| JP | 2350803 | * | 12/2000 |
| JP | 2017209688 | * | 11/2017 |

OTHER PUBLICATIONS

Haji, Abdirehman, et al. "Overcoming Hazards in Sour Gas Sampling By Controlled Measures", SPE-183058-MS International, Society of Petroleum Engineers. Nov. 7, 2016, pp. 1-9 (9 pages).

* cited by examiner

*Primary Examiner* — Jamel E Williams
*Assistant Examiner* — Alex T Devito
(74) *Attorney, Agent, or Firm* — Osha Bergman Watanabe & Burton LLP

(57) ABSTRACT

A method for identifying a sample includes collecting a sample in a sample cylinder, directing the sample from the sample cylinder to a tube with controlled pressure, and identifying a phase, a color, and existence of impurities of the sample through a transparent portion of the tube.

4 Claims, 1 Drawing Sheet

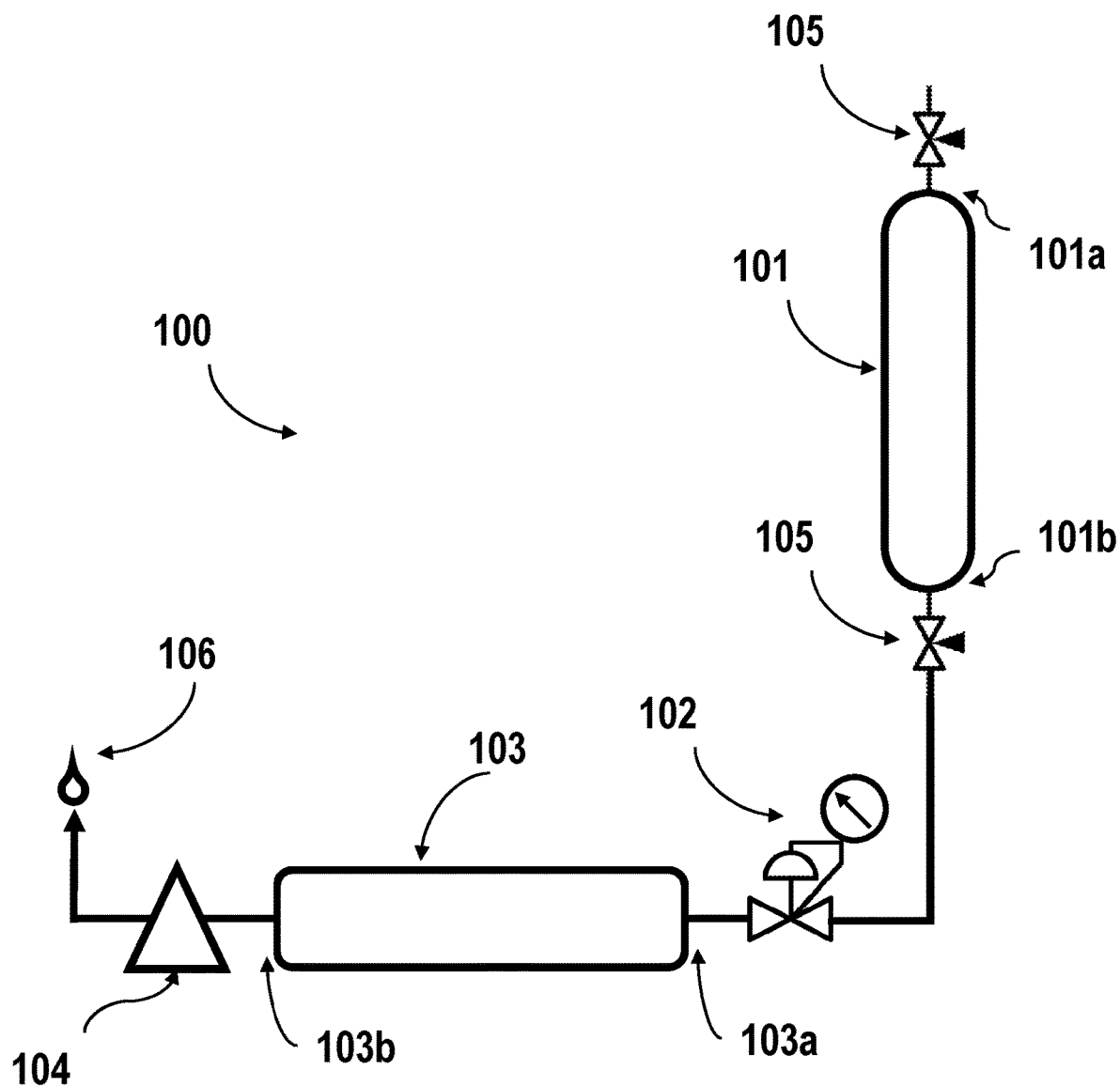

SAMPLE CYLINDER CONTENT IDENTIFICATION SYSTEM AND METHOD THEREOF

BACKGROUND

Hydrogen sulfide ($H_2S$) is a toxic, colorless, and flammable gas with a rotten egg odor, and is a common component in natural gas and other hydrocarbon-bearing reservoirs having gaseous or liquid hydrocarbon content. Samples from oil and gas wells, with which the hydrogen sulfide is associated, are often transferred to a research laboratory for compositional analysis using a sample cylinder. Study of the hydrogen sulfide in the content of the samples support safe and effective exploration and production activities as well as the protection of personnel that work with and around such gases.

More importantly, researching and understanding appearance of the samples provides useful information for screening and classification of the samples prior to further analysis and is critical to appreciate the quality of the samples to guide further analysis. As such, a system and a method allowing simple, fast, and reliable identification of these aspects of the samples are desired.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method for identifying a sample comprising: collecting a sample in a sample cylinder; directing the sample from the sample cylinder to a tube with controlled pressure; and identifying a phase, a color, or existence of impurities of the sample through a transparent portion of the tube.

Other aspects and advantages of this disclosure will be apparent from the following description made with reference to the accompanying drawings and the appended claims.

BRIEF DESCRIPTION OF DRAWINGS

Certain embodiments of the disclosure will be described with reference to the accompanying drawings, where like reference numerals denote like elements. It should be understood, however, that the accompanying FIGURES illustrate the various implementations described and are not meant to limit the scope of various technologies described.

The FIGURE shows a system according to one or more embodiments.

In the present disclosure including the FIGURES, down are toward or at the bottom and up are toward or at the top of the FIGURE. "Up" and "down" are generally oriented relative to a local vertical direction. However, "upstream" may more generally refer to objects, units, or processes, taken before a particular unit or process. As well, "downstream" may more generally refer to objects, units, or processes, taken after a particular unit or process.

DETAILED DESCRIPTION

In the following, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

One or more embodiments of the present disclosure relate to a method for identifying a content of a sample using a system shown in the figure. The system 100 may comprise one or more of a sample cylinder 101, a pressure control system 102, an identification tube 103, and a detector 104.

According to one or more embodiments of the present disclosure, the sample cylinder 101 refers to a container that temporarily stores a sample, for example, when transferring the sample off-site to another location (such as a laboratory) for further analysis. The content in the sample cylinder (or the sample) may be collected from an oil and gas well or an oil and gas plant. The sample may contain solids, liquids, gases, or any combination thereof. The sample may contain hydrocarbons having a carbon chain length ranging from C1 to C9+, carbon dioxide, oxygen, hydrogen sulfide, water, etc., with its composition dependent on its source and conditions. In one or more embodiments, the sample may be a liquefied petroleum gas or a natural gas. In one or more embodiments, the sample may be in a form of slurry, emulsion, foam, or mist. The sample cylinder 101 may have two ends: a first end and a second end. The sample cylinder 101 may have a first opening 101a at the first end and a second opening 101b at the second end. In one or more embodiments, the first opening of sample cylinder 101a may be used to collect the sample. The second opening of the sample cylinder 101b may connect to the pressure control system 102.

The system 100 may comprise one or more valves 105. In one or more embodiments, the valves may be used to control a flow to or from the sample cylinder 101. The one or more valves may be a one-way valve. As used herein, the term "one-way valve" is directed to a device that allows a fluid to enter a space within an enclosed area in one direction, but does not independently allow the fluid to exit the space in a reverse direction. The one-way valve may have a release mechanism whereby a person can activate the mechanism thereby causing at least some of the fluid within the sample retaining space to flow out of the enclosed area. However, the one-way valve should be designed such that any fluid that enters the space will not freely flow back out of that space without external intervention. The one-way valve may be positioned at the first opening of the sample cylinder 101a, controlling introduction of the sample into the sample cylinder. In this manner, the sample may remain inside the sample cylinder until such time when it is desirable to remove the sample from the sample cylinder. The one-way valve may be positioned at the second opening of the sample cylinder 101b, controlling the sample out of the sample cylinder. Alternatively, the one or more valves may be a two-way valve. In one or more embodiments, the one or more valves may be associated with one or more seal. In one or more embodiments, the one or more valves may comprise a rupture disc. In one or more embodiments, there may be one or more valves disposed between other components in the system, to control the flow of the sample through the whole system.

According to one or more embodiments of the present disclosure, the system 100 may comprise a pressure control system 102. The pressure control system 102 may be coupled upstream or downstream of the sample cylinder 101 in a manner such that the pressure of a flow of the sample passing through the pressure control system is detectable. For example, as shown in the FIGURE, pressure control system 102 is configured as part of system 100 and is positioned between the sample cylinder 101 and the identification tube 103. Under such configuration, the pressure control system 102 may be used for high-sensitivity pressure control of a sample flow from the sample cylinder 101 to the identification tube 103. The pressure control system 102 controls and maintains sample pressure for safety reasons, for monitoring a phase change of the sample at different stage of pressure, and for maintaining the sample quantity from lost for further analysis. The pressure control system 102 may control a pressure in a range of from 0 psig to about 1000 psig, depending on a desired pressure of the flow into the identification tube. In one or more embodiments, the pressure control system 102 may comprise a pressure indicator and a pressure regulator. In one or more embodiments, the pressure control system 102 may perform pressure control such that a pressure of the sample flow is at a same level as a pressure in the sample cylinder. Alternatively, the pressure control system 102 may perform pressure control such that the pressure of the sample flow is lower than the pressure in the sample cylinder. In the case of reducing pressure, the pressure control system 102 may be connected to a flaring system to vent at least a part of the sample.

According to one or more embodiments of the present disclosure, the system may comprise an identification tube 103 for visual identification of the sample. For example, as shown in the FIGURE, the system 100 may comprise an identification tube 103 positioned downstream to the pressure control system. The identification tube 103 may have an inlet 103a and an outlet 103b. The sample may be introduced into the identification tube at the inlet 103a, with the sample flow having a pressure controlled by the pressure control system 102. The outlet 103b may allow the sample to be removed from the identification tube. At least a part of the identification tube 103 is at least partially transparent, such that the content inside the identification tube is visible from outside the identification tube to visually identify one or more characteristics of the sample. The identification tube 103 may enable visual identification on whether the sample is in liquid phase or gas phase. The identification tube 103 may enable visual identification on whether the sample is clear or contains impurities. For example, the identification tube may enable identification of black particles, oily sludge, the presence of water, an unusual color, or any other content or impurities that cause changes to the physical and/or chemical properties of the sample. The impurities may be present due to manufacturing processes, degradation, storage conditions, handling procedures, transportation, or contamination, for example. The impurities may affect sample integrity, personal & instrument safety, as well as the environment. Visual identification helps to detect these impurities prior to further analysis of the sample, for example, using a spectrometer. The sample may also be classified prior to analysis, such that a proper spectroscopic method or procedure is selected.

In one or more embodiments, the transparent part of the identification tube may be comprised of glass, such as quartz glass. The glass tube may be a high-pressure glass tube that bears pressure to a certain degree, depending on materials, thicknesses, and end finishes of the glass tube. In one or more embodiments, the identification tube may comprise a transparent window comprised of a high-pressure glass, where the rest of the identification tube can be made of other materials. The identification tube may bear high pressure, for example at a same level of the pressure in the sample cylinder.

According to one or more embodiments of the present disclosure, the system may comprise one or more detectors. For example, as shown in the FIGURE, the system 100 may comprise a detector 104 to determine a level of hydrogen sulfide in the sample flow. The detector 104 may be positioned downstream to the identification tube, such that the detector 104 determines the level of hydrogen sulfide in a flow of sample from the identification tube. The detector may be integrated with the identification tube, for example, by inserting at least a part of the detector into the identification tube. The detector may be any type of hydrogen sulfide detector, such as gold film sensors, colorimetric gas detection tubes, electrochemical cells, or lead acetate cassette tapes. In one or more embodiments, the detection range of the detector may be from 0 ppm (parts per million) to about 1000 ppm, and may vary based on make and model of the hydrogen sulfide detector. The detector may provide information on the quality of the sample, for example, to determine whether the sample contains sour gas or sweet gas. Sour gas refers to a gas containing a large amount of hydrogen sulfide. Usually, the gas is categorized as sour gas if it contains more than 5.7 mg of hydrogen sulfide per cubic meter, which is equivalent to 4 ppm by volume. Sweet gas refers to a gas containing trace amount of hydrogen sulfide and carbon dioxide, which is non-corrosive in its pure form and requires little refining. Because the sour gas may cause corrosion to pipelines and containers, and because hydrogen sulfide is toxic, a step of sweetening is normally required to remove hydrogen sulfide from the gas. In other words, the sour gas requires conversion into sweet gas which is suitable and safe for transportation and sale, and the detector provides information with regard to whether a sweetening process is necessary. The detection results may also be used in sample classification and provide guidance based on capability and specifications of laboratory instruments to a certain detection limit.

According to one or more embodiments of the present disclosure, the system may further comprise a flare system 106. The sample flow may be directed to the flare system and purged without exposure or emission to atmosphere.

The sample flow may also be directed to a spectrometer for compositional analysis of the sample. For example, the spectrometer may be a gas chromatography (GC) with a detection system, which may include, for example, a flame ionization detector (FID), a pulsed flame photometric detector (PFPD), or a thermal conductivity detector (TCD).

According to one or more embodiments, the system of the present disclosure may further comprise fittings, seals, and/or tubings to connect one or more aforementioned members in the system without leakage of hydrogen sulfide or other gaseous and/or liquid species present in the sample. The fittings may be used to connect the one or more members of the system in a variety of ways. For example, the fittings may be threaded with a male end, or a female end, or both. The fittings and tubings may be comprised of a material that is inert to hydrogen sulfide, for example, polymers, glass, and stainless steel with coating. The seals may be positioned at each end of one or more members of the system described herein.

One or more embodiments of the present disclosure may relate to a method using the system disclosed herein. The method may comprise collecting a sample in a sample cylinder. The sample may be collected from an oil and gas well or an oil and gas plant, and may contain solids, liquids, gases, or any combination thereof. The sample may contain hydrocarbons having a carbon chain length ranging from C1 to C9+, carbon dioxide, oxygen, hydrogen sulfide, water, etc., with its composition dependent on its source and conditions. The sample may be collected through a first opening of the sample cylinder.

In one or more embodiments, the method may comprise directing the sample from the sample cylinder to a tube with controlled pressure. The pressure may be controlled by a pressure control system described herein. The tube may be an identification tube as described herein. At least a portion of the tube is at least partially transparent, such that the sample content inside the tube is visible from outside the tube. For example, the pressure may be controlled to be at a same level of the sample inside the sample cylinder, so as to identify one or more characteristics of the sample under such pressure. The pressure may be controlled to be at a lower level then a pressure inside the sample cylinder so as to identify one or more characteristics of the sample under low pressure. The pressure may be controlled to increase over a phase change pressure of the sample, such that the sample in a gas phase transform to a liquid phase. Alternatively, the pressure may be controlled to decrease over a phase change pressure of the sample by guiding a portion of the sample to a flare system, such that the sample in a liquid phase transform to a gas phase. Under such phase change, a color and existence of the sample may be identified.

In one or more embodiments, the method may comprise identifying one or more characteristics of the sample through a transparent portion of the tube. For example, the identifying may provide characteristics information on whether the sample is gas, liquid, slurry, emulsion, foam, or mist at controlled pressure. The identifying may provide characteristics information on whether the sample is colorless, has an unusual color, or contains water, oily sludge, or impurities. The characteristics information may be used to guide screening and further analysis of the sample.

In one or more embodiments, the method may further comprise screening the sample based on the one or more characteristics of the sample. For example, when an unusual color or impurities (such as black particles) are visually identified, the sample may be screened due to possible contamination. In one or more embodiments, when the sample is in gas phase, the sample may be screened if presence of water, oily sludge, or emulsion is identified. In one or more embodiments, the sample may be filtered or pretreated prior to further analysis using instrumentations if presence of water, oily sludge, or emulsion is identified. In one or more embodiments, the characteristics information may be used to guide further analysis. For example, if impurities, unusual color, water, or oily sludge are present, the sample may require a pretreatment or filtration prior to further spectroscopic analysis, so as to protect the instruments from damages or contamination. In one or more embodiments, if impurities, unusual color, water, or oily sludge are present, the sample may be discarded. If no impurities, unusual color, water, or oily sludge is identified, the sample may proceed for further analysis, for example, using a gas chromatography or other instrumentation of interest.

In one or more embodiments, the method may further comprise detecting a level of hydrogen sulfide of the sample. In one or more embodiments, the method may further comprise classifying the sample based on the level of hydrogen sulfide, for example, based on different concentrations of hydrogen sulfide or based on whether the sample is a sour gas or a sweet gas. The classification results may provide essential guidance for further analysis of the sample, for example, in selecting suitable instruments and parameters. A sour gas may contain more than 5.7 mg of hydrogen sulfide per cubic meter of gas (for example, natural gas), which is equivalent to 4 ppm by volume. When the sample is classified as a sour gas, the sample may be diluted for analysis, and detection parameters of a gas chromatography may be adjusted to a higher range. In one or more embodiments, the detector used for gas chromatography may be selected based on sweet or sour gas. For example, the TCD detector may be used to measure hydrogen sulfide, carbon dioxide, light hydrocarbons, and compounds that respond poorly to the FID detector, and may be used to analyze sour gas. The FID detector may be used to detect the presence of organic compounds including hydrocarbons and volatile organic compounds, such as the sweet gas. Further, the PFPD detector may be used to analyze sulfur species and hydrogen sulfide in ppm levels, which is applicable to only sweet gas.

The system and method disclosed herein may be used in oil and gas applications, for example, to classify a sample based on its characteristics, to provide guidance for compositional analysis to prevent damage to instruments, and to effectively avoid risk of exposure of toxic gases. The system and method enable identification hydrogen sulfide within a short period of time, for example, few seconds.

Unless defined otherwise, all technical and scientific terms used have the same meaning as commonly understood by one of ordinary skill in the art to which these systems, apparatuses, methods, processes, and compositions belong.

Ranges may be expressed as from about one particular value to about another particular value, inclusive. When such a range is expressed, it is to be understood that another embodiment is from the one particular value to the other particular value, along with all particular values and combinations thereof within the range.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method for identifying a sample comprising:
   collecting a sample in a sample cylinder;
   directing the sample from the sample cylinder to a tube, using a pressure control system disposed between the sample cylinder and the tube, such that a pressure in the tube is at a same level as a pressure in the sample cylinder;
   identifying a phase of the sample and increasing the pressure in the tube to observe phase change of the sample;
   identifying whether or not oily sludge or black particles exist in the sample through a transparent portion of the tube;

analyzing the sample using gas chromatography if neither oily sludge nor black particles are identified through the transparent portion of the tube, and filtering the sample if oily sludge and/or black particles are identified through the transparent portion of the tube.

2. The method of claim 1, further comprising detecting a level of hydrogen sulfide of the sample in the tube.

3. The method of claim 2, further comprising classifying the sample as containing a sweet gas or a sour gas based on the level of hydrogen sulfide.

4. The method of claim 1, further comprising:

analyzing the filtered sample using gas chromatography after filtering the sample.

* * * * *